US011804076B2

(12) United States Patent
Abdel-Malek et al.

(10) Patent No.: US 11,804,076 B2
(45) Date of Patent: Oct. 31, 2023

(54) SYSTEM AND METHOD FOR THE AUTONOMOUS IDENTIFICATION OF PHYSICAL ABUSE

(71) Applicant: University of Iowa Research Foundation, Iowa City, IA (US)

(72) Inventors: Karim Abdel-Malek, Coralville, IA (US); Kimberly Farrell, Iowa City, IA (US); Rajan M. Bhatt, Coralville, IA (US); Daniel L. Clay, Iowa City, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 438 days.

(21) Appl. No.: 17/061,980

(22) Filed: Oct. 2, 2020

(65) Prior Publication Data
US 2021/0100481 A1    Apr. 8, 2021

Related U.S. Application Data

(60) Provisional application No. 62/909,649, filed on Oct. 2, 2019.

(51) Int. Cl.
G06V 40/20      (2022.01)
A61B 5/11       (2006.01)
(Continued)

(52) U.S. Cl.
CPC .............. *G06V 40/20* (2022.01); *A61B 5/117* (2013.01); *A61B 5/1114* (2013.01);
(Continued)

(58) Field of Classification Search
CPC ...... G06V 40/20; G06V 20/52; G06V 10/422; G06V 40/103; A61B 5/1114;
(Continued)

(56) References Cited

U.S. PATENT DOCUMENTS 3,936,822 A    2/1976  Hirschberg
5,790,685 A    8/1998  Sallee
(Continued)

FOREIGN PATENT DOCUMENTS

CN    101692284 A    4/2010
JP    2014-071871 A  4/2014
WO    2009/061283 A2 5/2009

OTHER PUBLICATIONS

Datta et al. 'Person-on-Person Violence Detection in Video Data'; 1051-4651/02 2002 IEEE; pp. 433-438; 2002 (Year: 2002).*
(Continued)

Primary Examiner — Patrick Fernandes
(74) Attorney, Agent, or Firm — Smith, Gambrell & Russell, LLP

(57) ABSTRACT

Embodiments of the present systems and methods may provide techniques that may provide the capability to autonomously and automatically identify cases of suspected abuse, which may then be subject to follow up review and action. For example, in an embodiment, a system for identifying potential physical abuse in a location may comprise at least one video camera provided at the location and a computer system comprising a processor, memory accessible by the processor, and computer program instructions stored in the memory and executable by the processor to cause the computer system to perform: receiving video data from the at least one video camera, identifying potential physical abuse from the video data, the identification being to within a predetermined confidence level, and transmitting information indicating that a potential human threat has been identified.

8 Claims, 10 Drawing Sheets

(51) Int. Cl.
  *A61B 5/117* (2016.01)
  *A61B 5/00* (2006.01)
  *G06V 10/422* (2022.01)
  *G06V 20/52* (2022.01)
  *G06V 40/10* (2022.01)

(52) U.S. Cl.
  CPC .......... *A61B 5/1122* (2013.01); *A61B 5/1128* (2013.01); *A61B 5/48* (2013.01); *G06V 10/422* (2022.01); *G06V 20/52* (2022.01); *G06V 40/103* (2022.01)

(58) Field of Classification Search
  CPC ..... A61B 5/1122; A61B 5/1128; A61B 5/117; A61B 5/48; H04W 12/06; H04N 23/66; G06T 7/80; G06T 7/246; G06T 7/20; B64D 47/08
  See application file for complete search history.

(56) References Cited

U.S. PATENT DOCUMENTS

| | | | |
|---|---|---|---|
| 5,917,775 | A | 6/1999 | Salisbury |
| 6,243,106 | B1 | 6/2001 | Rehg et al. |
| 6,256,418 | B1 | 7/2001 | Rehg et al. |
| 6,269,172 | B1 | 7/2001 | Rehg et al. |
| 6,281,792 | B1 | 8/2001 | Lerg et al. |
| 7,336,999 | B1 | 2/2008 | Koh |
| 8,965,044 | B1 | 2/2015 | Owechko et al. |
| 9,710,708 | B1 | 7/2017 | Checka |
| 10,445,930 | B1* | 10/2019 | Saylor ................. G06T 7/80 |
| 10,919,152 | B1 | 2/2021 | Kalouche |
| 2001/0007452 | A1 | 7/2001 | Naka et al. |
| 2008/0129581 | A1 | 6/2008 | Douglass et al. |
| 2008/0152192 | A1 | 6/2008 | Zhu et al. |
| 2009/0182524 | A1 | 7/2009 | Stephanson |
| 2009/0245573 | A1* | 10/2009 | Saptharishi ............ H04N 23/66 382/103 |
| 2011/0148875 | A1 | 6/2011 | Kim et al. |
| 2011/0267344 | A1 | 11/2011 | Germann et al. |
| 2012/0162217 | A1 | 6/2012 | Lim et al. |
| 2013/0230211 | A1 | 9/2013 | Tanabiki et al. |
| 2013/0293686 | A1 | 11/2013 | Blow et al. |
| 2014/0147014 | A1 | 5/2014 | Mallet et al. |
| 2014/0336848 | A1 | 11/2014 | Saund et al. |
| 2015/0085133 | A1 | 3/2015 | Teich et al. |
| 2016/0140818 | A1 | 5/2016 | Viviani |
| 2016/0232774 | A1 | 8/2016 | Noland et al. |
| 2016/0291700 | A1 | 10/2016 | Geisner et al. |
| 2016/0377381 | A1 | 12/2016 | Lyren |
| 2018/0272992 | A1 | 9/2018 | Gage et al. |
| 2018/0322680 | A1 | 11/2018 | McElmurray et al. |
| 2019/0116322 | A1 | 4/2019 | Holzer et al. |
| 2019/0154401 | A1 | 5/2019 | Almagor et al. |
| 2019/0172223 | A1 | 6/2019 | Vajda et al. |
| 2020/0137357 | A1* | 4/2020 | Kapoustin ............. H04W 12/06 |
| 2020/0142580 | A1* | 5/2020 | Shao ..................... B64D 47/08 |

OTHER PUBLICATIONS

U.S. Department of Education—Web Tables, "Student Reports of Bullying and Cyber-Bullying: Results from the 2011 School Crime Supplement to the National Crime Victimization Survey," Institute of Educational Sciences, NCES 2013-329, Aug. 2013, 52 pages.

Centers for Disease Control and Prevention, Morbidity and Mortality Weekly Report, "Youth Risk Behavior Surveillance—United States, 2013," U.S. Department of Health and Human Services, Surveillance Summaries, vol. 63, No. 4, Jun. 2014, 172 pages.

Bradshaw, C.P., et al., "Bullying and Peer Victimization at School: Perceptual Differences Between Students and School Staff," School Psychology Review, 36:3, 361-382 (2007).

Krug, E.G., et al., "The World Report on Violence and Health," The Lancet, vol. 360(9339), 1083-1088, Oct. 2002.

Salend, E., et al., "Elder Abuse Reporting: Limitations of Statutes," The Gerontologist, vol. 24, No. 1, 61-69 (1984).

Verma, Gyanendra K., et al. A Handheld Gun Detection using Faster R-CNN Deep Learning. ICCCT—2017 Proceedings of the 7th International Conference on Computer and Communication Technology. 2017. pp. 84-88.

Wiggers, Kyle. Athena Security uses computer vision to detect guns and other weapons. 2018. Accessed Apr. 1, 2019. https://venturebeat.com/2018/09/27/athena-security-uses-computer-vision-to-detect-guns-and-other-weapons/.

Singleton, Mitchell, et al. Gun Identification Using Tensorflow. Social Informatics and Telecommunications Engineering. ICST Institute for Computer Sciences. 2018, L. Meng and Y. Zhang (Eds.). MLICOM 2018, LNICST 251, pp. 3-12.

Lai, Justin. Developing a Real-Time Gun Detection Classifier. Lecture Notes of the Institute for Computer Sciences, Social Informatics and Telecommunications Engineering book series (LNICST, vol. 251). 2018. 4 pages.

Hsu, Jeremy. New in School: AI-Driven Gun Detection Systems. 2018. 5 pages. Accessed Apr. 1, 2019. https://undark.org/article/new-in-school-ai-driven-gun-detection-systems/.

Olmos, Roberto, et al. Automatic Handgun Detection Alarm in Videos Using Deep Learning. Neurocomputing, vol. 275. 2018, pp. 66-72.

Lee, Mun Wai et al. A model-based approach for estimating human 3D poses in static images. IEEE Transactions on Pattern Recognition and Machine Intelligence. 2006. vol. 28, No. 6, pp. 905-916.

Gavrila, D.M. et al. 3-D model-based tracking of humans in action: A multi-view approach. Proceedings of IEEE Computer Society Conference on Computer Vision and Pattern Recognition. 1996. pp. 73-80.

Kapsouras, Ionnis et al. Action Recognition in Motion Capture Data Using a Bag of Postures Approach. 22nd International Conference on Pattern Recognition. 2014. pp. 2649-2654.

Perez-Sala, Xavier et al. A Survey on Model Based Approaches for 2D and 3D Visual Human Pose Recovery. Sensors. 2014. vol. 14(3), pp. 4189-4210.

Hunter. E. A. et al. Estimation of Articulated Motion Using Kinematically Constrained Mixture Densities. Proceedings IEEE Nonrigid and Articulated Motion Workshop. 1997. pp. 10-17.

Abdel-Malek, Karim A. Human Motion Simulation: Predictive Dynamics. El Sevier. 2013. 281 Pages.

* cited by examiner

Optimization Formulation
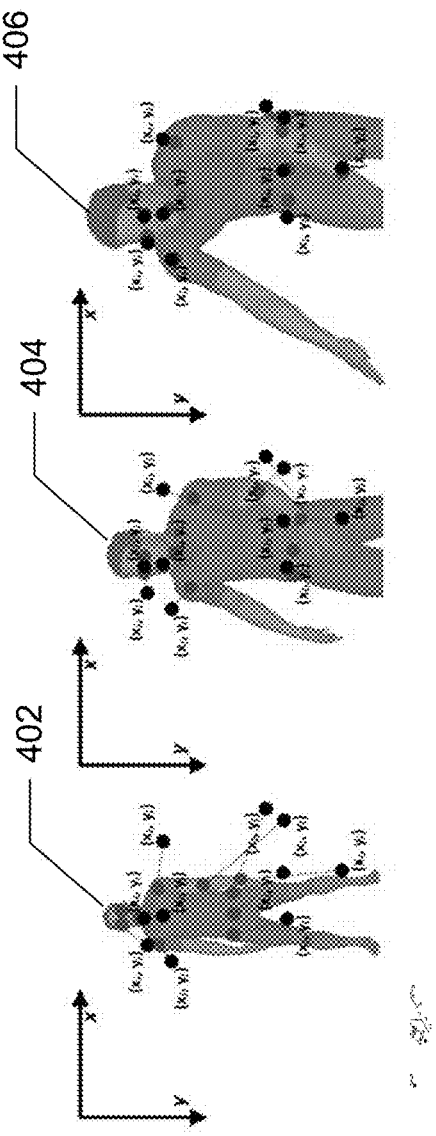
Uses the DH kinematic structure → Drives the posture of the spatial model to minimize the distances
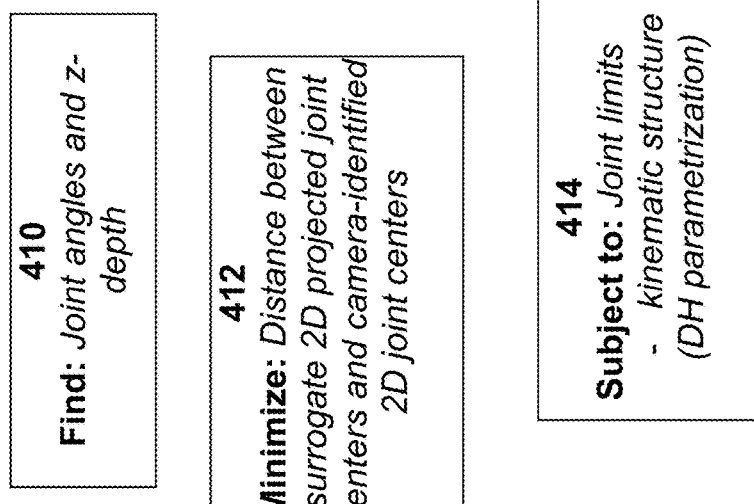
410 Find: *Joint angles and z-depth*
412 Minimize: *Distance between surrogate 2D projected joint centers and camera-identified 2D joint centers*
414 Subject to: *Joint limits – kinematic structure (DH parametrization)*
← 314
FIG. 4

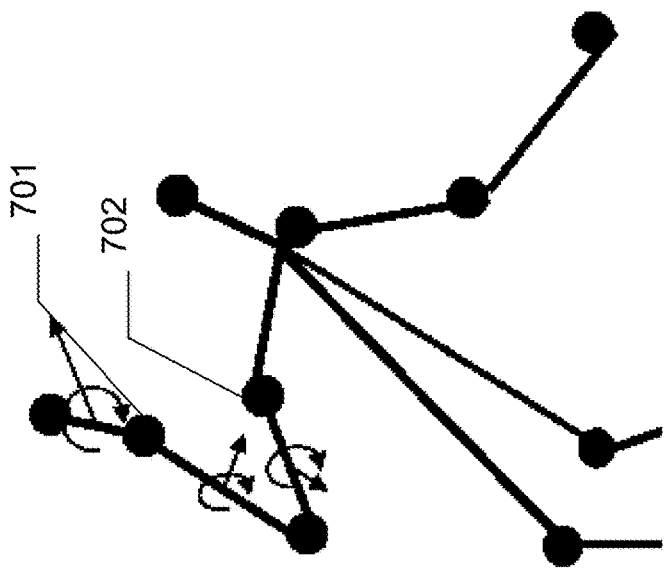
FIG. 7

SYSTEM AND METHOD FOR THE AUTONOMOUS IDENTIFICATION OF PHYSICAL ABUSE

CROSS-REFERENCE TO RELATED APPLICATIONS

This application claims the benefit of U.S. Provisional Application No. 62/909,649, filed Oct. 2, 2019, which is incorporated by reference herein in its entirety.

BACKGROUND

The present invention relates to systems and methods that may provide the capability to autonomously and automatically identify cases of suspected abuse, which may then be subject to follow up review and action.

Physical abuse has been a widespread problem for some time. For example, child abuse, school bullying, elder/senior abuse, etc., are common types of abuse. While legal definitions of child abuse vary from state to state, physical abuse is one of the most common forms of child maltreatment. Physical abuse occurs when a parent or caregiver commits an act that results in physical injury to a child or adolescent, such as red marks, cuts, welts, bruises, muscle sprains, or broken bones, even if the injury was unintentional.

Likewise, one of the most common types of abuse is school bullying. Sexual, verbal, emotional, and cyber bullying are examples of school bullying. Of particular focus is the type of bullying that occurs with physical abuse in schools.

Further, while there are many types of reported elderly abuse, including physical, verbal/mental, financial, sexual, and neglect, of particular concern is physical abuse. Physical abuse is characterized by a force intended to cause unnecessary injury or pain to a person. This can be anything from severe beatings to physical or chemical restraining, for example. Other forms of physical abuse include but are not limited to kicking, pushing, pinching, slapping, shoving, burning, biting, and drowning. Physical abuse can be unintentional—someone may intend to help the elder but the behavior can still be considered abusive if the action(s) taken embody any of the above.

Typical methods currently employed in detecting physical abuse rarely use technological methods, but may include factors such as clinical manifestations, having well-known risk factors, questions answered by or statements made by a person, and security surveillance cameras, whether in public areas, such as schools, or in secret, such as in suspected child or elder abuse.

While these techniques may provide some deterrence, unfortunately studies show that many cases of abuse largely go unnoticed and unreported. Most abused persons, such as children and the elderly, do not or cannot report the abuse. Video recordings of an incident would only be effective if the recordings are reviewed. However, it is simply not possible to review surveillance footage for hours, days, and months following an incident. Equally important is the fact that often times the abused is unable to inform or report on the abuse because of being scared, physically unable, or a combination of factors.

Accordingly, a need arises for techniques that may provide the capability to autonomously and automatically identify cases of suspected abuse, which may then be subject to follow up review and action.

SUMMARY

Embodiments of the present systems and methods may provide techniques that may provide the capability to autonomously and automatically identify cases of suspected abuse, which may then be subject to follow up review and action. Embodiments may provide a novel and effective methodology to capture and track human/soldier behavior, characteristic of extended and complex motion, using a Spatial Posture and Motion Identification (SPMI) method. Embodiments of SPMI may be based on the utilization of a single mono camera, coupled with deep-learning algorithms to capture behavior/motion, derive the 2D kinematics of the captured motion, and then impose the 2D kinematics to the 3D human model (SANTOS).

Embodiments may provide a powerful system to obtain spatial 3D kinematics of the human body. Embodiments may use an approach that first calibrates the segment link lengths of the body, then employ a deep-learning algorithm to identify body segments (2D) of the individual, and culminate with the application of an optimization approach to calculate the joint centers of the motion with the kinematic skeleton.

Embodiments may take a standard 2D video of human movement and estimate the kinematic motion and biomechanics on a 3D human model. Using optimization and a widely-accepted mathematical human model, 3D motion may be estimated from just one stationary camera. First, machine learning algorithms may identify and track 2D joint center positions on at least one person in the video input. These 2D joint positions may then be used as input and drive the motion solver, which may predict the motion on a 3D human model as joint angles over time. These joint angles may be used with existing models for biomechanical analysis.

Embodiments of the present systems and methods may utilize technology for motion tracking of people using a single camera and transferring this motion to a full kinematic model of a human being. Embodiments may use the Santos human model, which is represented by 215 degrees of freedom. The skeleton of the Santos model allows for natural behavior by predicting postures, also called inverse kinematics. However, these posture predictions require the input of the coordinates of an end-effector. In the case of a 2D image from a camera, the human is projected onto a 2D image. From that image, at best, we can calculate or estimate the joint centers. Note that no markers or sensors on the body are needed for this process.

Embodiments may calculate a specific posture by projecting the 2D image onto the 3D human skeleton. In embodiments, the joint centers from the model may be obtained from pixels from a video stream. Then line segments may be identified, the line segments may be connected, the joint centers may be projected onto the SANTOS human model, and then the virtual model may be sized to be as close as possible to the human. Motion of the human may be tracked in real-time in order to identify postures and motions that may indicate the occurrence of physical abuse.

For example, in an embodiment, a system for identifying potential physical abuse in a location may comprise at least one video camera provided at the location and a computer system comprising a processor, memory accessible by the processor, and computer program instructions stored in the memory and executable by the processor to cause the computer system to perform: receiving video data from the at least one video camera, identifying potential physical abuse from the video data, the identification being to within a predetermined confidence level, and transmitting information indicating that a potential human threat has been identified.

In embodiments, the identifying may be performed by: tracking and modeling bodily motion of at least one person shown in the video data, quantifying velocity and acceleration of at least one portion of a body of the at least one person shown in the video data using the tracked and modeled bodily motion, and determining potential physical abuse based on the quantified velocity and acceleration of at least one portion of a body of at least one person shown in the video data. The tracking and modeling bodily motion of at least one person shown in the video data may be performed by: identifying and tracking 2D joint center positions of the at least one person shown in the video data and predicting motion of at least one portion of a body of the at least one person shown in the video data on a 3D human model as joint angles of the person over time. The predicting motion of at least one portion of a body may comprise: connecting 2D joint center positions of the at least one person shown in the video data to form line segments. Determining potential physical abuse may comprise comparing quantified velocity and acceleration of at least one portion of a body of the at least one person shown in the video data with at least one threshold. The at least one portion of the body may comprise at least one of a wrist, a shoulder, and an elbow.

In an embodiment, a method for identifying potential physical abuse may be implemented in a computer comprising a processor, memory accessible by the processor, and computer program instructions stored in the memory and executable by the processor, and the method may comprise: receiving video data from at least one video camera at a location, identifying potential physical abuse from the video data, the identification being to within a predetermined confidence level, and transmitting information indicating that a potential human threat has been identified.

BRIEF DESCRIPTION OF THE DRAWINGS

The details of the present invention, both as to its structure and operation, can best be understood by referring to the accompanying drawings, in which like reference numbers and designations refer to like elements.

FIG. 4 shows an exemplary process of optimizing to find joint angles and z-axis depths.

FIG. 7 illustrates an example of motion tracking, according to embodiments of the present systems and methods.

DETAILED DESCRIPTION

Figure 1:
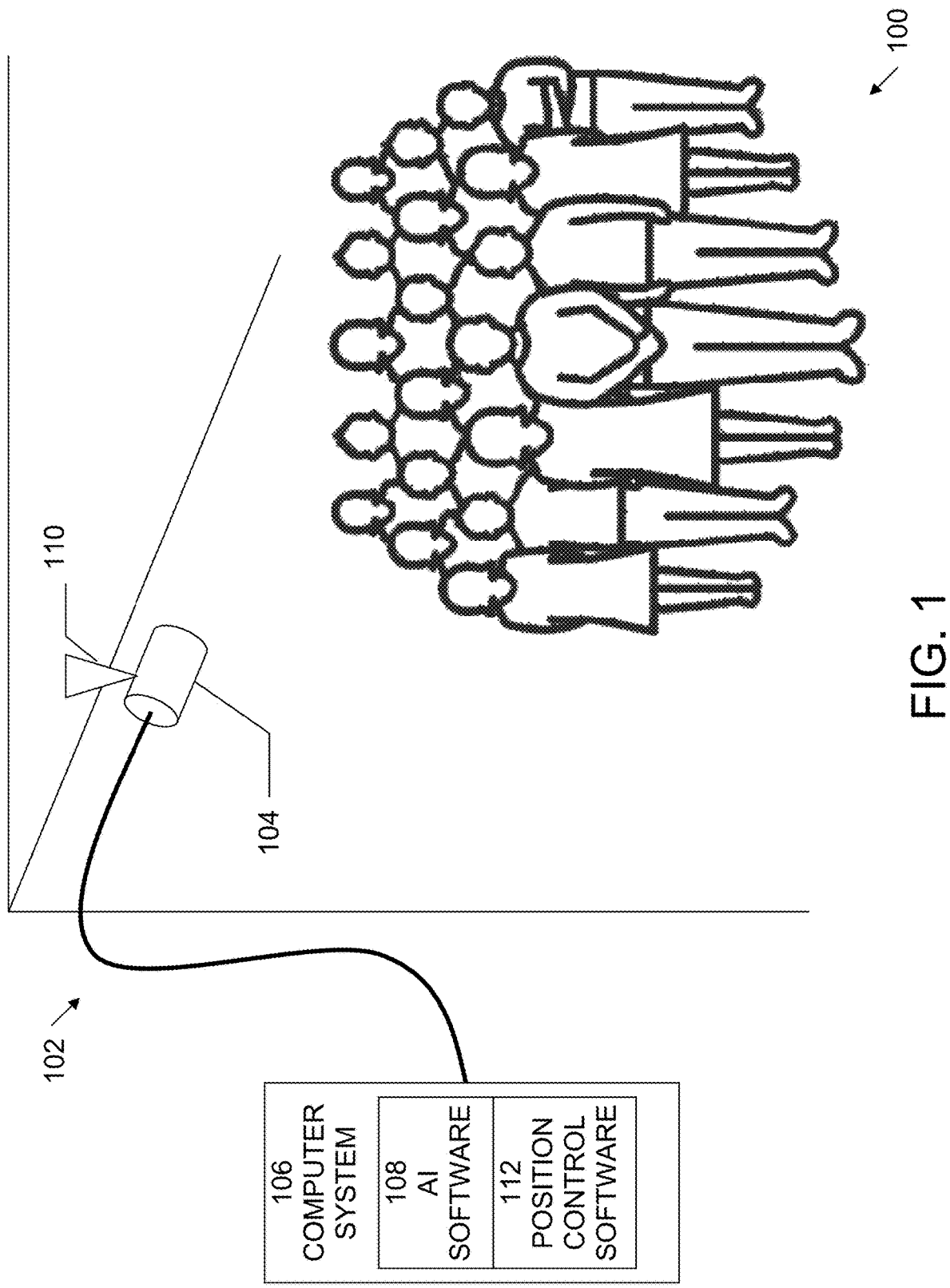
FIG. 1 shows an exemplary environment in which embodiments of the present systems and methods may be implemented.

One of ordinary skill in the art will appreciate that the disclosure provided herein is exemplary and that alternative components can be used within the disclosed method and device. Therefore, all such alternatives should be considered as being included herein.

Embodiments of the present systems and methods may provide techniques that may provide the capability to autonomously and automatically identify cases of suspected abuse, which may then be subject to follow up review and action. Embodiments of the present systems and methods may utilize technology for motion tracking of people using a single camera and transferring this motion to a full kinematic model of a human being. Embodiments may use the Santos human model, which is represented by 215 degrees of freedom. The skeleton of the Santos model allows for natural behavior by predicting postures, also called inverse kinematics. However, these posture predictions require the input of the coordinates of an end-effector. In the case of a 2D image from a camera, the human is projected onto a 2D image. From that image, at best, we can calculate or estimate the joint centers. Note that no markers on the body are needed for this process.

Embodiments may calculate a specific posture by projecting the 2D image onto the 3D human skeleton. In embodiments, the joint centers from the model may be obtained from pixels from a video stream. Then line segments may be identified, the line segments may be connected, the joint centers may be projected onto the SANTOS human model, and then the virtual model may be sized to be as close as possible to the human. Motion of the human may be tracked in real-time in order to identify postures and motions that may indicate the occurrence of physical abuse Embodiments of the present systems and methods may provide benefits such as:

Inexpensive: with the advent of camera and surveillance technologies in almost every business, the embodiments may include a software product.

No human interaction: Monitoring by humans is time consuming. There cannot be a security officer at every nursing home, not to mention at every private home where the elderly may receive care. Embodiments of the present systems and methods may operate without human interaction.

Monitors 24/7: Embodiments may operate during day and night conditions (with infrared security cameras) and can work 24/7.

A deterrent: knowledge that surveillance monitoring of abuse exists may act as a deterrent for potential perpetrators Low maintenance: Embodiments may include few components, such as a camera and a computer or computing device, and as such should not need significant maintenance Easy to use: Embodiments may operate autonomously and should not require active monitoring.

Leverages current surveillance systems: Surveillance cameras are ubiquitous. Embodiments may leverage existing cameras to obtain streaming video capture and process in real-time.

Scalable to other types of physical abuse: While only a few types of physical abuse have been identified, embodiments may be scaled and adopted for use in other physical abuse situations.

Single camera: Embodiments may provide for full 3D reconstruction of the human body during motion and the ability to recreate avatars in a quick manner from a single camera.

Physics-based: Because the re-created motion is a simulation and not an animation, it enables a physics based to be applied.

Avatar configuration: Because the re-created motion is a simulation, the virtual character can now be configured with load including equipment, clothing, helmet, etc.

Predictive human behavior: The simulations created using the SPIN integrated into SANTOS enables cause and effect. Human motion may be affected by load, terrain, environment, and human behavior will accordingly be reactive.

Identification of physical abuse.

An exemplary environment 100 in which embodiments of the present systems and methods may be implemented is shown in FIG. 1. In this example, a system 102 for identifying potential abuse is shown in an indoor environment. It is to be noted that an indoor environment is merely an example of an environment in which embodiments of the present system may be implemented. Such examples may include classrooms, offices, hospital rooms, conference rooms, auditoriums, theaters, etc. While for simplicity this disclosure may refer to indoor environments, it is to be noted that embodiments of the present systems and methods are not limited to such locations. Rather, embodiments of the present systems and methods may be implemented in any location or environment as desired.

Exemplary environment 100 includes an exemplary embodiment of a system 102 for identifying potential physical abuse. As shown in this example, system 102 may include one or more cameras 104, such as a wide angle camera, a computer system 106, artificial intelligence (AI) software 108, a gimbal (pan and tilt) motorized system 110, and a position feedback control system 112. Cameras 104 may include one or more cameras, which may have similar or different fields of view, such as wide-angle, telephoto, etc. Cameras 104 may be image sensors of different modalities, such as thermal cameras, depth (three-dimensional) cameras, etc.

Computer system 106 may run the software needed to perform embodiments of the present methods. Although for clarity, computer system 106 is shown separate from the remainder of system 102, embodiments may include computer system 106 with the remainder of system 102 or embodiments may include computer system 106 separate from, but communicatively connected to, the remainder of system 102 (or built in) or integrated therein. Computer system 106 may include AI software 108 and position control software 112. AI software 108 may perform potential shooter recognition, as described below. Position control software 112 may interact with position sensors and motors in gimbal system 110 to control the movement and position of cameras 104. Gimbal system 110 may include a motorized pan and tilt gimbal and may include position and other sensors.

Figure 2:
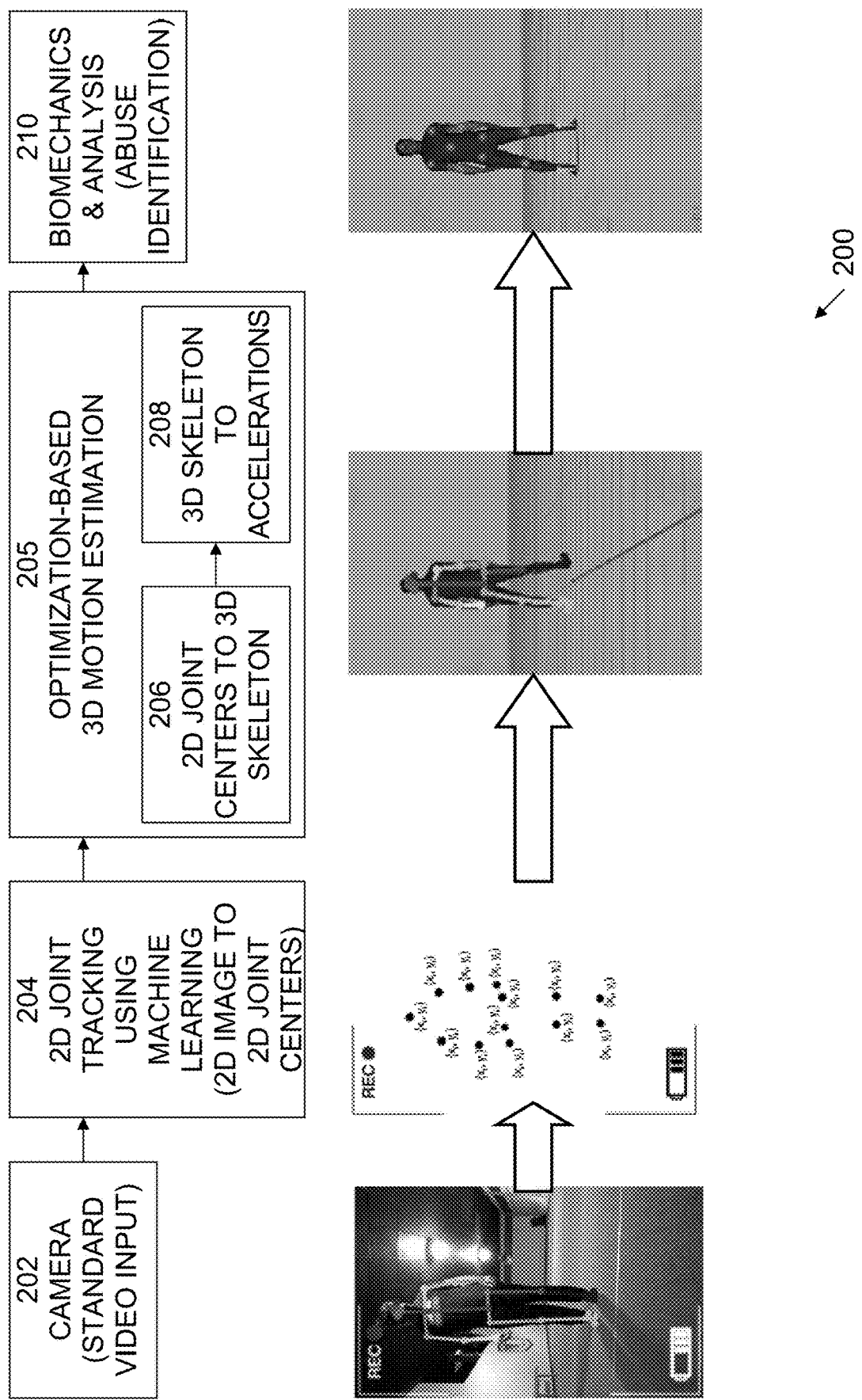
FIG. 2 shows an exemplary block diagram of processing blocks that may be included in embodiments of the present systems and methods.

An exemplary block diagram of processing blocks 200 that may be included in embodiments of the present systems and methods is shown in FIG. 2. As shown in this example, there is a camera 202, 2D image to 2D joint centers processing 204, optimization-based 3d motion estimation (motion solver) 205 including 2D joint centers to 3D skeleton processing 206, 3D skeleton to accelerations processing 208, and abuse identification processing 210. In embodiments, the processing may take as input a standard 2D video of human movement from camera 202 and may estimate the kinematic motion and biomechanics on a 3D human model. Using optimization and a widely-accepted mathematical human model, 3D motion may be estimated from just one stationary monoscopic camera. At 304 machine learning algorithms may identify and track 2D joint center positions 404 on at least one person in the video input. At 306 these 2D joint positions may then be used as input and drive the motion solver, (2D joint centers to 3D skeleton processing 206), which may predict the motion of body portions on a 3D human model as joint angles 406 of the person over time. These joint angles may be used with existing models for biomechanical analysis. At 208, the 3D skeleton model may be processed to determine velocities and accelerations. At 210, the 3D skeleton model, along with the velocities and accelerations of body portions of the person, may be processed to identify abuse.

In embodiments, 2D joint centers to 3D skeleton processing 206 may involve connecting joint centers appearing on the 2D image to form line segments. The segment lengths may be in relation to the posture of a body in the video. An arm segment, for example, in 3D when projected onto a 2D image may appear significantly shorter.

The motion solver itself constitutes a unique process by which estimates human motion from 2D screen positions over time. For each frame in the video of the motion, the 2D screen positions of the joint centers are considered as input. Let us assume that $p_d$ is the vector of the desired input 2D screen positions of all joint centers such that $$p_d = [\{x_1, y_1\}, \{x_2, y_2\}, \ldots \{x_n, y_n\}]^T \qquad (1)$$

where $\{x_i, y_i\}$ $i=1 \ldots n$ are then joint center locations. The joint centers of the virtual 3D human avatar in the virtual environment are projected on a virtual camera that corresponds to the actual camera used to record the motion. The vector of projected coordinates of the camera is assumed to be $p_a$ where $$p_a = [\{x_1^a, y_1^a\}, \{x_2^a, y_2^a\}, \ldots \{x_n^a, y_n^a\}]^T \qquad (2)$$

$\{x_i^a, y_i^a\}$ $i=1 \ldots n$ are the coordinate pairs of corresponding joints on the virtual avatar projected on the virtual camera in the 3D environment. The vector $p_a = f(q)$ where $q = [q_1\ q_2 \ldots q_m]^T$ a vector of all m joint angles of the virtual human model needed to calculate the kinematics as in Equation (3) below. Thus, the joint centers from the 3D human model are converted into virtual 2D screen positions. The difference between the positions of the 2D joint center screen positions given as input and their virtual counterparts projected on virtual camera is calculated as $d = f(p_d, p_a)$.

Figure 9:
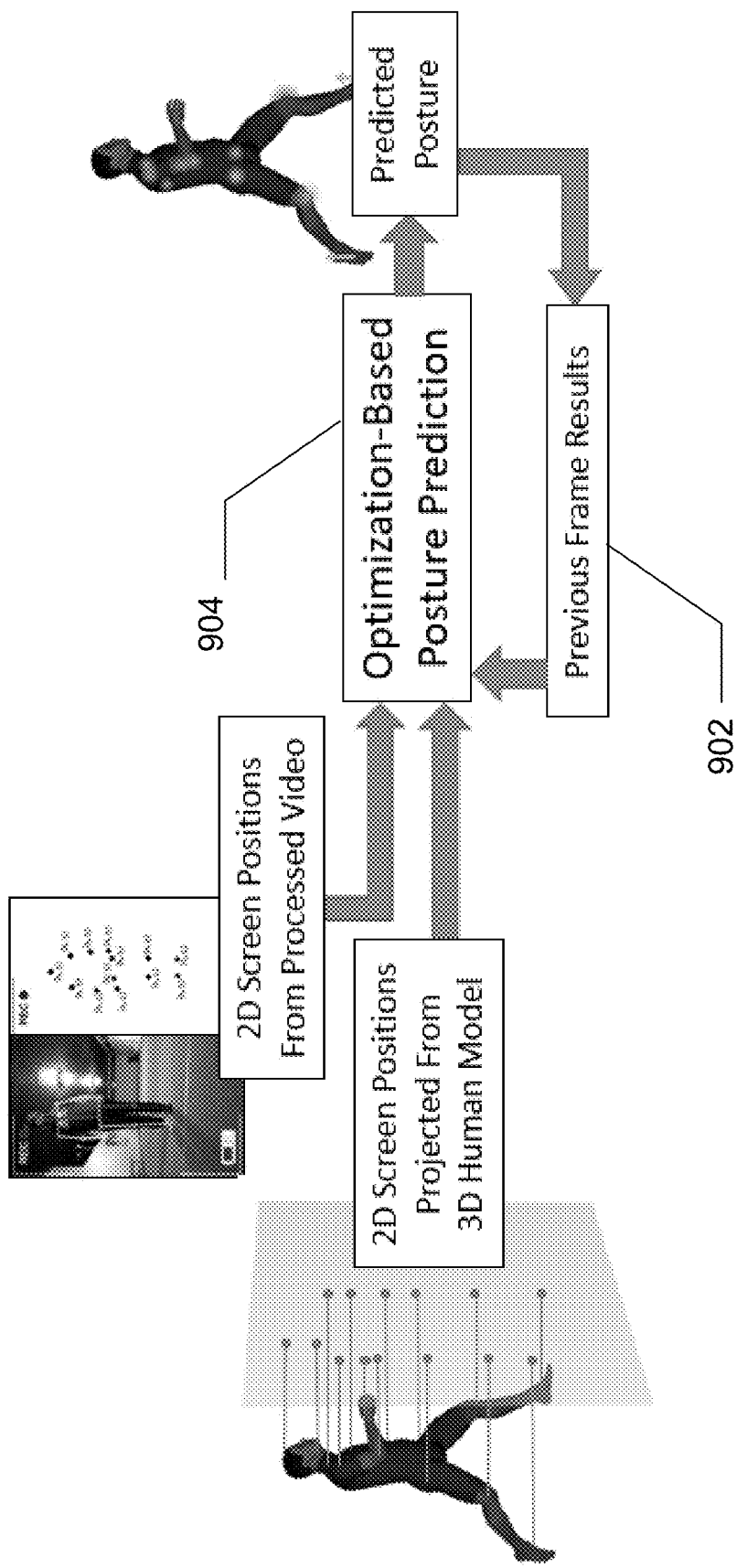
FIG. 9 illustrates an example of motion tracking of people from a single camera.

The optimization-based spatial posture identification problem determines the optimal kinematic posture so that this distance d is minimized, resulting in a posture that is like the posture of the human subject in the video. Such optimization problem can be formulated as below:

Determine q by
Minimizing $d^T d$
Subject to $q_j^L \leq q_j \leq q_j^U$ $j=1 \ldots m$ where $q_j^L$ is the lower limit and is the upper limit of the joint $q_j$. This process results in many potential solutions, and it is possible for the identified 3D posture to vary from the actual posture. As shown in FIG. 9, to minimize this error in identified posture and keep the motion smooth, the previous frames 902 may be considered and used to guide the optimization process 904 to a more likely posture. Once the 3D posture and thus 3D motion is estimated, further analysis yields a better estimate of the pose of the person.

Figure 3A:
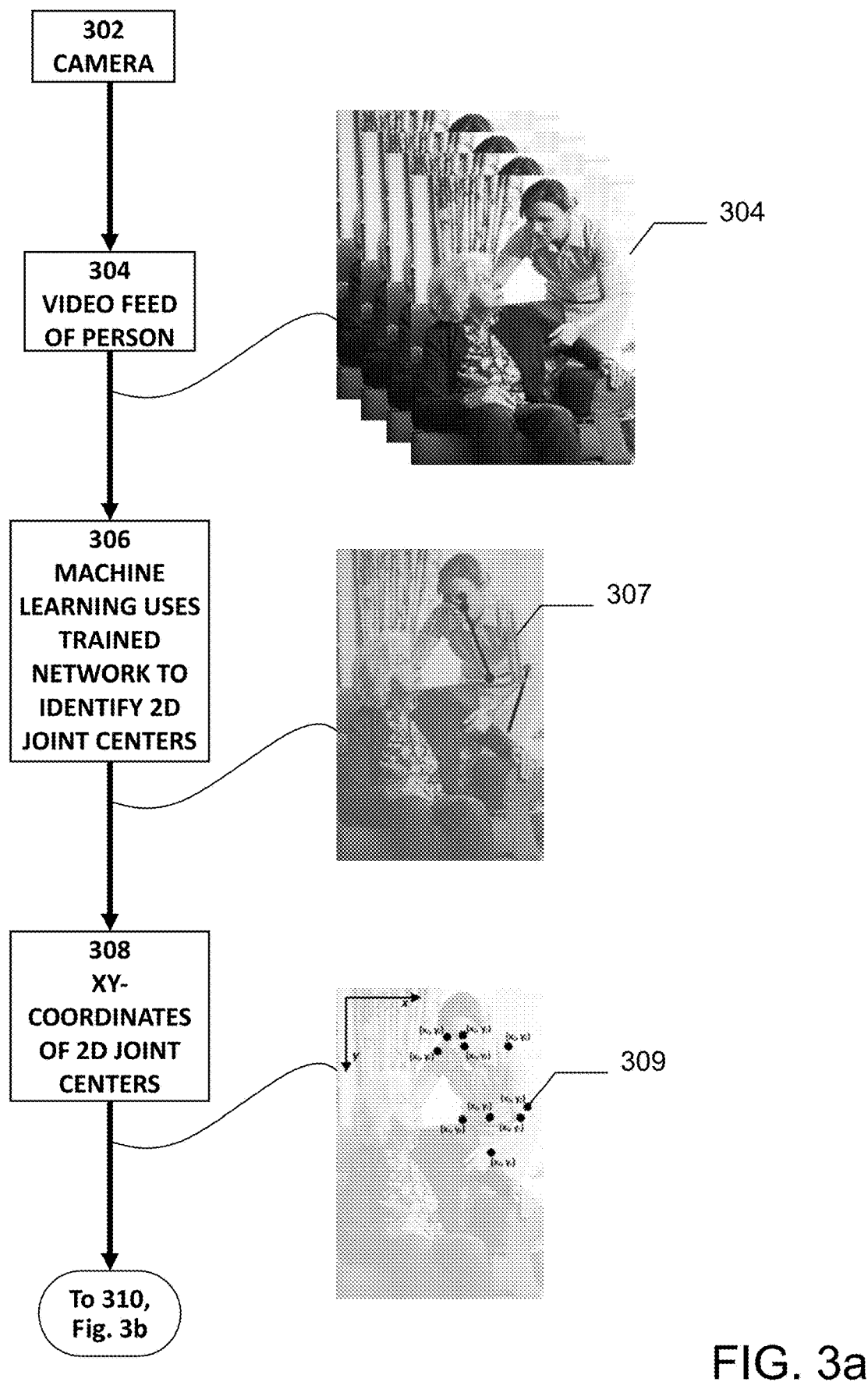
FIGS. 3a, 3b show an exemplary process of motion tracking of people from a single camera, according to embodiments of the present systems and methods.
Figure 3B:
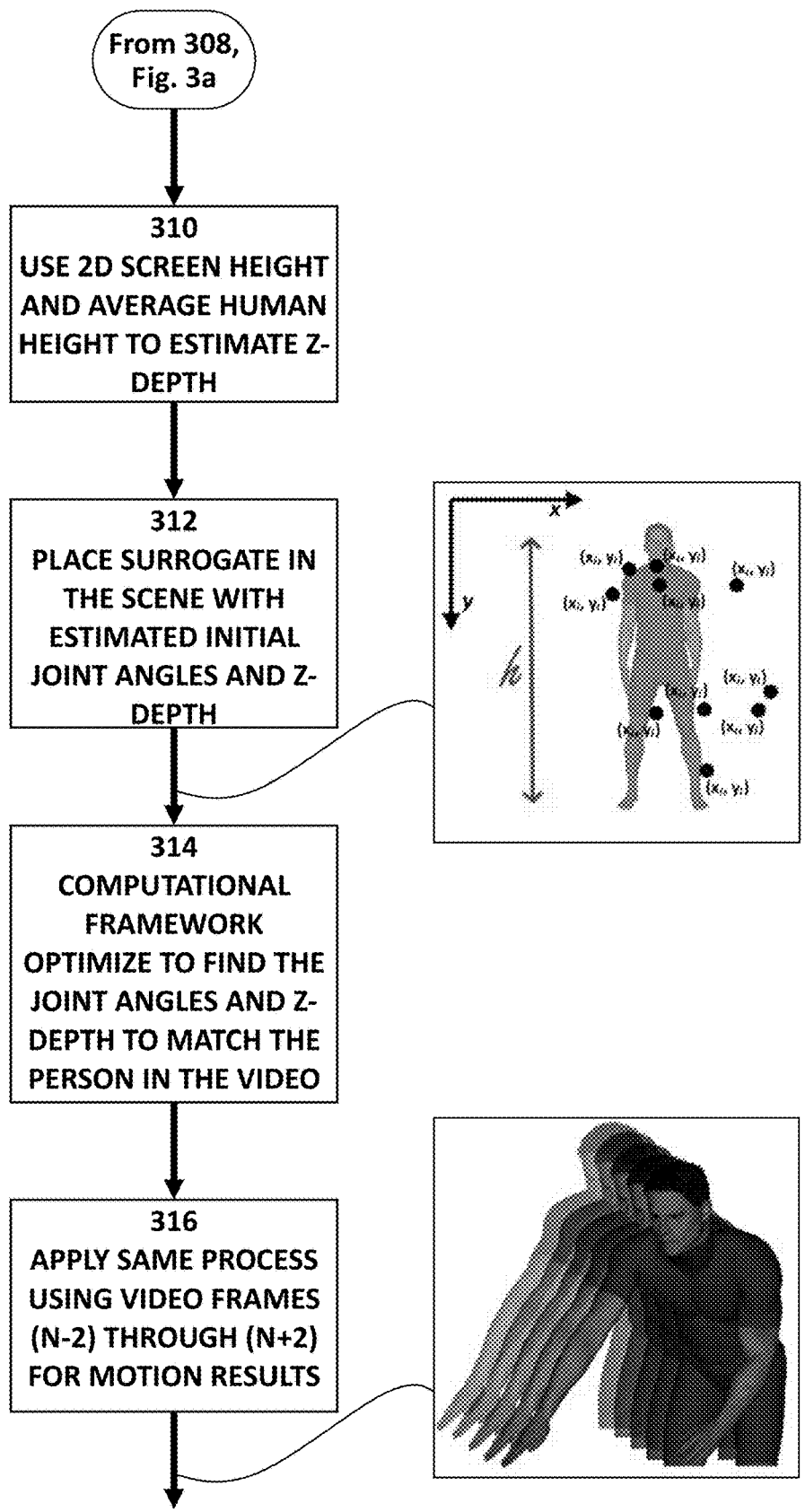

Embodiments may provide a unique, and potentially transformational, means by which a simple video sequence can be analyzed and mapped to a much more sophisticated, and much more useful, 3D model, from which physiological and biomechanical metrics can be obtained to quantitatively assess the entirety of the motion sequence. Once defined in the physics-based 3D model and simulation, the avatar can be varied to represent any number of anthropometric body types, and the precise motion sequence simulated repeatedly to capture variability of performance metrics resulting from variability in soldier physiology. The captured movements are converted into 3D skeleton models and then adapted into the most appropriate avatar Processing 204 and 206 may provide estimates of human motion from 2D screen positions over time. An example of such processing 300 is shown in FIGS. 3a and 3b. For example, as shown in FIG. 3a, a camera 302 may provide a 2D video feed or image stream of a person 304. For each frame in the video of the person, at 306, a trained machine learning model, such as a neural network, may be used to identify the 2D joint centers 307. At 308, the xy-coordinates 309 of the 2D joint centers 307 may be determined. Turning now to FIG. 3b, at 310, the height of the image of the person in the 2D image and the average height of a human may be used to estimate the z or depth axis dimensions of the 2D joint centers. At 312, a spatial model figure may be generated and placed in the scene and configured using estimated initial joint angles and the estimated z-axis depth generated at 310. At 314, a computational framework may be used to optimize the spatial model configuration to find joint angles and the z-axis depths to match the person in the 2D video image stream. At 316, 302-314 may be repeated for additional frames, for example, for the two following frames and the two preceding frames, so as to provide motion results.

An example of optimization processing that may be performed at 314 of FIG. 3 is shown in FIG. 4. At 410, processing 314 may utilize a computational framework, such as the Denavit-Hartenberg kinematic structure to optimize the spatial model configuration to find joint angles and the z-axis depths to match the person in the 2D video image stream. At 412, the distances between the 2D projected joint centers of the spatial model 402 and the camera-identified 2D joint centers 404 may be minimized 406, so that the spatial model may be configured to substantially match the person in the 2D video image stream. Iteration on this process may drive the posture of the spatial model to minimize these distances. At 414, it is noted that the configuration is subject to certain constraints, such as the limits of joint movement and the kinematic structure of the body.

Figure 5:
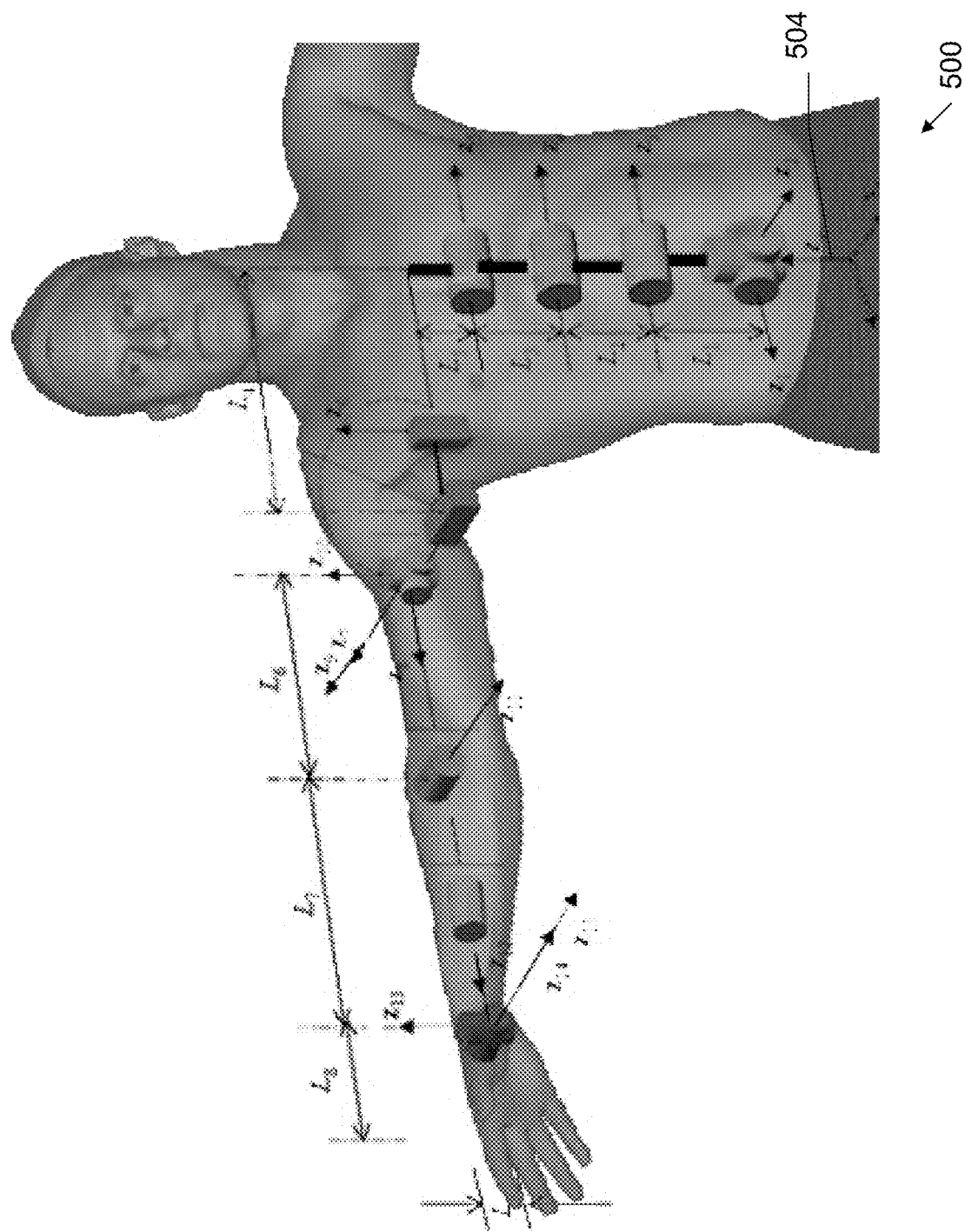
FIG. 5 shows exemplary upper extremity modeling, according to embodiments of the present systems and methods.

In embodiments, each extremity may be modeled using a methodology such as that described by Abdel-Malek and Arora (2013). (Abdel-Malek, K., & Arora, J. S. (2013). *Human Motion Simulation: Predictive Dynamics*. Academic Press.) For example, the upper extremity is shown in FIG. 5. This method uses a systemic modeling methodology to build the skeleton of the human. The modeling methodology 600 is shown more clearly in FIG. 6.

In embodiments, the location of the origin of the first coordinate frame (frame 0) may be chosen to be anywhere along the $z_0$ axis 602. In addition, for the $n^{th}$ coordinate system, it can be chosen to be embedded anywhere in the $n^{th}$ link subject to the above four rules as constraints on the relationships between the axes:
(a) the $x_n$-axis is perpendicular to both the $z_{n-1}$ and $z_n$ axes
(b) the $x_n$-axis intersects both $x_n$ and $z_n$ axes
(c) the origin of joint n is at the intersection of $x_n$ and $z_n$
(d) The $y_n$ completes a right-handed reference frame based on $x_n$ and $z_n$.

In order to generate the matrix relating any two links, four parameters may be needed. The four parameters may include 1) $\theta_i$—the joint angle, measured from the $x_{i-1}$ to the $x_i$ axis about the $z_{i-1}$ (right hand rule applies). For a prismatic joint $\theta_i$ is a constant. It is basically the angle rotation of one link with respect to another about the $z_{i-1}$. The parameter $\theta_i$ may be called the generalized variables and may be denoted by $q_i$ whereby the vector $q=[q_1 \ldots q_n]$ characterizes the set of variables needed to describe the position and orientation of the kinematic chain.

The other 3 variables may be obtained from the image scaling to the human model, and may include 2) $d_i$—the distance from the origin of the $(i-1)^{th}$ coordinate frame to the intersection of the $z_{i-1}$ axis with the $x_i$ axis along $z_{i-1}$ axis; 3) $a_i$—the offset distance from the intersection of the $z_{i-1}$ axis with the $x_i$ axis to the origin of the $i^{th}$ frame along $x_i$ axis (Shortest distance between the $z_{i-1}$ and $z_i$ axis); and 4) and $\alpha_i$—offset angle from $z_{i-1}$ axis to $z_i$ axis about the $x_i$ axis (right hand rule). Note that the relative Degree-of-Freedom (DOF) (angles) have already been determined by the above methodology for obtaining a posture from the 2D image.

Figure 6:
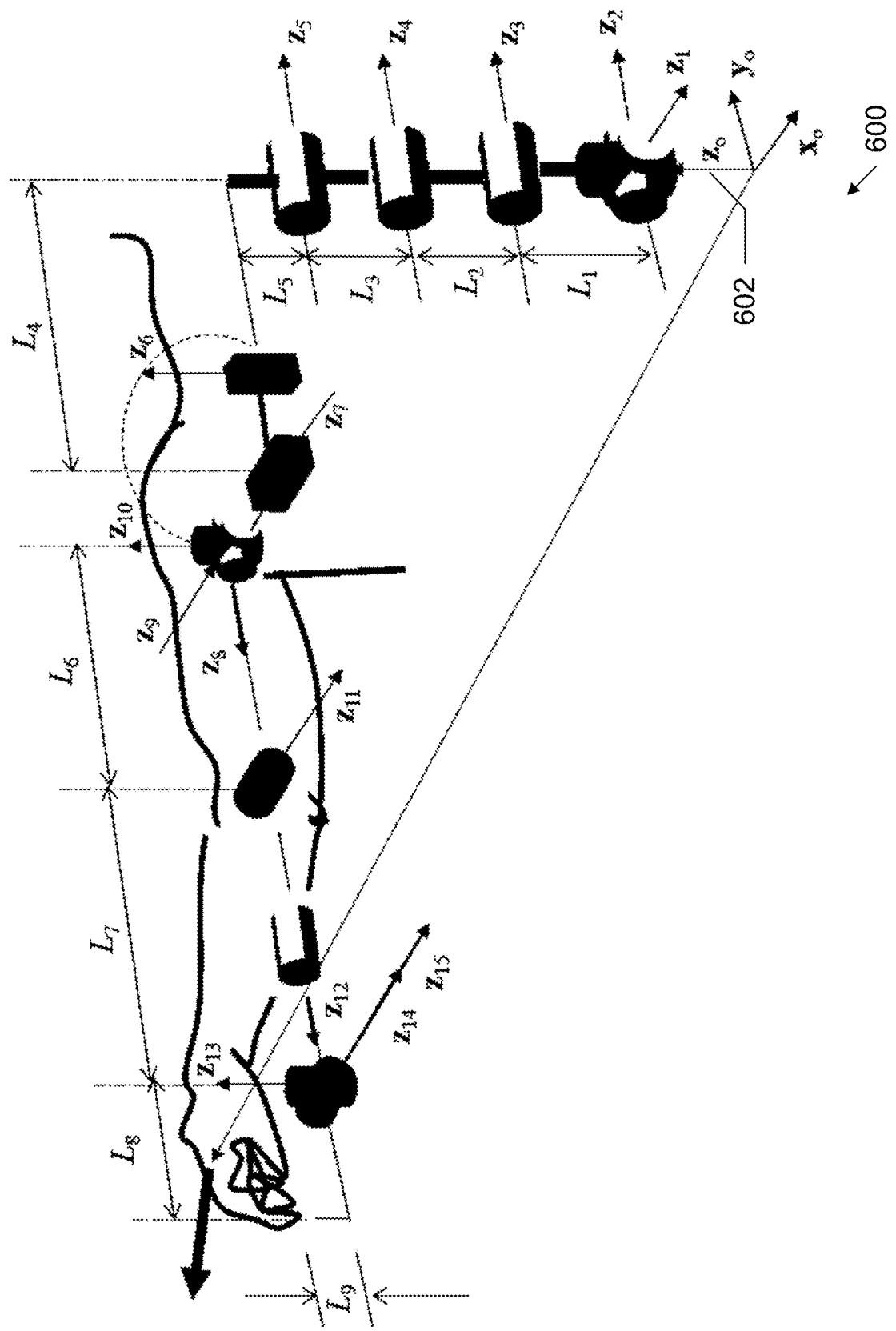
FIG. 6 shows exemplary upper extremity modeling, according to embodiments of the present systems and methods.

Each z-axis, starting with the first joint and denoted by $z_0$, is located along the joint, as shown in FIG. 6. The x-axis is also located but the y-axis is not shown to avoid cluttering the figure. The position and location of each axis determines the parameters $\theta_i, d_i, a_i, \alpha_i$, and hence, determine the resulting (4×4) homogeneous transformation matrix, Eq. (3).

$$^{i-1}T_i(q_i) = \begin{bmatrix} \cos q_i & -\cos\alpha_i \sin q_i & \sin\alpha_i \sin q_i & a_i \cos q_i \\ \sin q_i & \cos\alpha_i \cos q_i & -\sin\alpha_i \cos q_i & a_i \sin q_i \\ 0 & \sin\alpha_i & \cos\alpha_i & d_i \\ 0 & 0 & 0 & 1 \end{bmatrix} \quad (3)$$

Note that the above 4×4 matrix is now a function of only $q_i$.

For any sequence of consecutive transformations or for any serial mechanism, any two reference frames may be represented by the multiplication of the transformations between them. To relate the coordinates frames m−1 and m+n, the following transformations is computed $$^{m-1}T_m {}^m T_{m+1} \ldots {}^{m+n-1}T_{m+n} = {}^{m-1}T_{m+n} \quad (4)$$

In general, the kinematic equations of serial n-DOF segmental links relating the coordinates of the last link (the $n^{th}$ coordinate frame) with respect to the world coordinates system (the $0^{th}$ coordinate frame) can be written as $$^0T_i = {}^0T_1 {}^1T_2 \ldots {}^{i-1}T_i = \prod_{j=1}^{i} {}^{j-1}T_j \quad (5)$$

for $i = 1, 2, \ldots, n$

For example, for a 9 DOF model of the upper limb (n=9), the position and orientation of the 9th link with respect to the base frame (the first frame) is represented by:

$$^0T_1 {}^1T_2 \ldots {}^8T_9 = {}^0T_9 \quad (6)$$

If $^{m-1}x$ and $^m x$ are the extended position vectors of a point, referred to coordinate frames embedded in link m−1 and m, respectively, the relationship between the two vectors is given by $$^{m-1}x = {}^{m-1}T_m {}^m x \quad (7)$$

Similarly, a vector resolved in the coordinates of the hand ($^n v$) can be resolved in the world coordinate system by multiplying by the corresponding transformation matrix as $$^0 v = {}^0 T_n {}^n v \quad (8)$$

where the vector $^0 v$ is resolved in the world coordinate frame.

This $^0 v$ is the Cartesian velocity vector with respect to the generalized global frame, i.e., with respect to the ground.

The three components within the velocity vector are the true velocity component of the extremity end-effector.

In embodiments, each frame may be analyzed sequentially, and also the final velocity components may be compared to some pre-specified values stored therein.

3D skeleton to velocities and accelerations 208. Velocity and Acceleration Vectors. In order to obtain limb accelerations, the motion of every segmental link may be calculated. The acceleration of a rigid body, for example, may be characterized by two components, a linear acceleration vector of three components $a=[a_x, a_y, a_z]^T$ and an angular acceleration vector of three components $\alpha=[\alpha_x, \alpha_y, \alpha_z]^T$. Because of the unique representation of the kinematic model of the human, every limb can be tracked by these two components. To obtain the kinematics o (position, velocity, and acceleration) of each segmental link of the extremities, embodiments may utilize a spatial kinematic model of the human. The velocity at the origin the coordinate system of any segment is described by $$^0v_i = \left[\sum_{j=1}^{i} \frac{\partial^0 T_i}{\partial q_j} \dot{q}_j\right] {}^i r_i \qquad (9)$$

This velocity vector has three components. It has been determined that the value of the largest component is representative of the velocity affected during a punch, for example.

A similar expression for the angular velocity, linear acceleration, and angular acceleration may be obtained.

Example Thresholds. As embodiments may perform tracking in real-time, as shown in FIG. 7, the quantities and conditions described below may be effectively monitored and compared against specified limits. These limits may include thresholds of effective physical abuse, although they vary from one person to another. For example, thresholds that may be indicative of physical abuse may include velocity thresholds. For example, for a Reverse punch, the Peak resultant velocity at the wrist 701 may have a threshold of 2.5 m/s, while for a Lead punch, the Peak resultant velocity the wrist 701 may have a threshold of 2.7 m/s.

For example, a velocity coordination pattern for performing a reverse punch may have limits as follows:

| Reverse punch | Lead punch |
| --- | --- |
| Shoulder 702 1 m/s | Shoulder 702 0.7 m/s |
| Elbow 704 2 m/s | Elbow 704 1.8 m/s |

Likewise, an exemplary acceleration may be 2 g, or about 20 m/s$^2$.

Abuse identification. Embodiments may utilize a number of criteria to delineate whether physical abuse has occurred.

For example, the kinematics of the digital skeleton (position, velocity, and acceleration) may be calculated in real-time for the various body segments. By first identifying joint centers, the 2D image may be projected onto the 3D digital human model to track the motion of body segments. As a result, the system may enable the development of criteria for detecting limb accelerations that are typically manifested in specific physical altercations with another person and are characterized by significantly higher accelerations of body segments and an impact with another tracked person.

Identification of acceleration component values that are significantly different than every day values becomes readily available. Unfortunately, this event has to occur in order to be detected. Once it occurs, the system will flag the event and embodiments may provide options terms of alerting the appropriate authorities. Embodiments may, likewise, provide other options, such as starting a recording and sending that recording to the administration or authorities.

Physical Abuse Conditions. In embodiments, this type of physical abuse may be identified. Such abuse may be characterized by a significant movement of a limb of one person against another. Acceleration components of one limb are tracked and evaluated at all times. These conditions do not cover all types of physical abuse, nevertheless, they do encompass several of them.

Examples of relevant conditions that may be utilized by embodiments of the present systems and methods may include: 1) Two people identified in the frame; 2) One person in the vicinity of another; 3) Linear and angular velocities; 4) Linear accelerations of a limb above a specified norm; 5) Angular accelerations of a limb above a specified norm; and 6) Extremity of one person comes in contact (impacts) with another person. In embodiments, some or all of these conditions, or other conditions as well, may be used to identify physical abuse.

Figure 8:
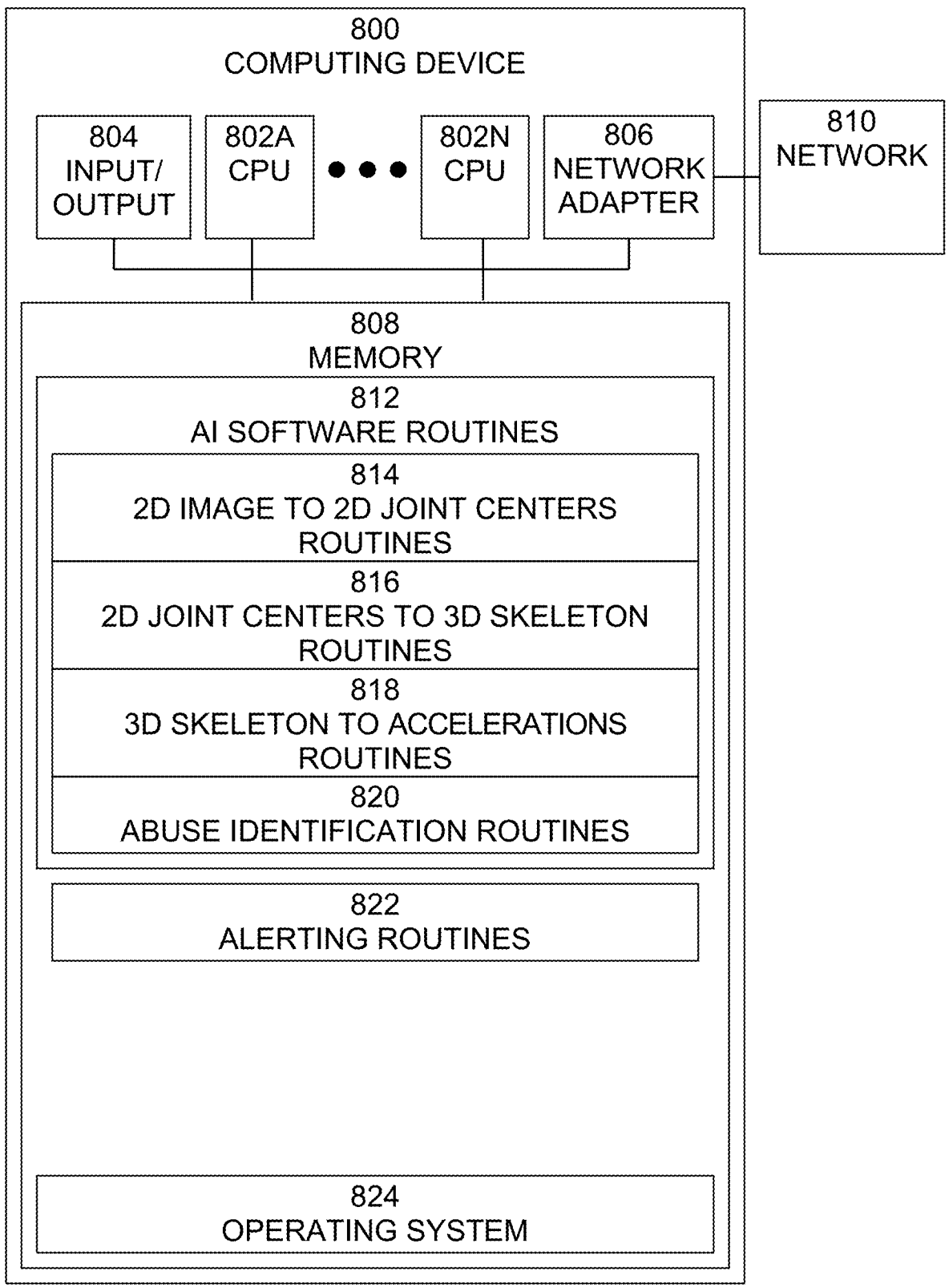
FIG. 8 shows an exemplary computer system according to embodiments of the present systems and methods.

An exemplary block diagram of a computer system 800, in which processes involved in the embodiments described herein may be implemented, is shown in FIG. 8. Computer system 800 may be implemented using one or more programmed general-purpose computer systems, such as embedded processors, systems on a chip, personal computers, workstations, server systems, and minicomputers or mainframe computers, or in distributed, networked computing environments. Computer system 800 may include one or more processors (CPUs) 802A-802N, input/output circuitry 804, network adapter 806, and memory 808. CPUs 802A-802N execute program instructions in order to carry out the functions of the present communications systems and methods. Typically, CPUs 802A-802N are one or more microprocessors, such as an INTEL CORE® processor. FIG. 8 illustrates an embodiment in which computer system 800 is implemented as a single multi-processor computer system, in which multiple processors 802A-802N share system resources, such as memory 808, input/output circuitry 804, and network adapter 806. However, the present communications systems and methods also include embodiments in which computer system 800 is implemented as a plurality of networked computer systems, which may be single-processor computer systems, multi-processor computer systems, or a mix thereof.

Input/output circuitry 804 provides the capability to input data to, or output data from, computer system 800. For example, input/output circuitry may include input devices, such as keyboards, mice, touchpads, trackballs, scanners, analog to digital converters, etc., output devices, such as video adapters, monitors, printers, etc., and input/output devices, such as, modems, etc. Network adapter 806 interfaces device 800 with a network 810. Network 810 may be any public or proprietary LAN or WAN, including, but not limited to the Internet.

Memory 808 stores program instructions that are executed by, and data that are used and processed by, CPU 802 to perform the functions of computer system 800. Memory 808 may include, for example, electronic memory devices, such as random-access memory (RAM), read-only memory (ROM), programmable read-only memory (PROM), electrically erasable programmable read-only memory (EE- PROM), flash memory, etc., and electro-mechanical memory, such as magnetic disk drives, tape drives, optical disk drives, etc., which may use an integrated drive electronics (IDE) interface, or a variation or enhancement thereof, such as enhanced IDE (EIDE) or ultra-direct memory access (UDMA), or a small computer system interface (SCSI) based interface, or a variation or enhancement thereof, such as fast-SCSI, wide-SCSI, fast and wide-SCSI, etc., or Serial Advanced Technology Attachment (SATA), or a variation or enhancement thereof, or a fiber channel-arbitrated loop (FC-AL) interface.

The contents of memory 808 may vary depending upon the function that computer system 800 is programmed to perform. In the example shown in FIG. 8, exemplary memory contents are shown representing routines and data for embodiments of the processes described above. However, one of skill in the art would recognize that these routines, along with the memory contents related to those routines, may not be included on one system or device, but rather may be distributed among a plurality of systems or devices, based on well-known engineering considerations. The present communications systems and methods may include any and all such arrangements.

In embodiments, at least a portion of the software shown in FIG. 8 may be implemented on a current leader server. Likewise, in embodiments, at least a portion of the software shown in FIG. 8 may be implemented on a computer system other than the current leader server.

In the example shown in FIG. 8, memory 808 may include AI software routines 812, which may include 2D image to 2D joint centers routines 814, 2D joint centers to 3D skeleton routines 816, and 3D skeleton to accelerations routines 818, abuse identification routines 820, alerting routines 822, and operating system 824. AI software routines 812 may include software routines to perform potential abuse recognition, as described above. 2D image to 2D joint centers routines 814 may include software routines, such as a machine learning routines, to identify and track 2D joint center positions on at least one person in a video input, as described above. 2D joint centers to 3D skeleton routines 816 may include software routines to predict the motion of the person on a 3D human model as joint angles over time, as described above. 3D skeleton to accelerations routines 818 may include software routines to determine velocities and accelerations of body portions of the person, as described above. Abuse identification routines 820 may include software routines to identify abuse using the 3D skeleton model, along with the velocities and accelerations of body portions of the person, as described above. Alerting routines 822 may include software routines to provide alarms, alerts, and notifications of potential abuse and their locations to authorities or administration, as described above. Operating system 824 may provide overall system functionality.

As shown in FIG. 8, the present communications systems and methods may include implementation on a system or systems that provide multi-processor, multi-tasking, multi-process, and/or multi-thread computing, as well as implementation on systems that provide only single processor, single thread computing. Multi-processor computing involves performing computing using more than one processor. Multi-tasking computing involves performing computing using more than one operating system task. A task is an operating system concept that refers to the combination of a program being executed and bookkeeping information used by the operating system. Whenever a program is executed, the operating system creates a new task for it. The task is like an envelope for the program in that it identifies the program with a task number and attaches other bookkeeping information to it. Many operating systems, including Linux, UNIX®, OS/2®, and Windows®, are capable of running many tasks at the same time and are called multi-tasking operating systems. Multi-tasking is the ability of an operating system to execute more than one executable at the same time. Each executable is running in its own address space, meaning that the executables have no way to share any of their memory. This has advantages, because it is impossible for any program to damage the execution of any of the other programs running on the system. However, the programs have no way to exchange any information except through the operating system (or by reading files stored on the file system). Multi-process computing is similar to multi-tasking computing, as the terms task and process are often used interchangeably, although some operating systems make a distinction between the two.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A system for identifying potential physical abuse in a location comprising:
   at least one video camera provided at the location; and
   a computer system comprising a processor, a memory accessible by the processor, and computer program instructions stored in the memory and executable by the processor to cause the computer system to perform:
   receiving video data from the at least one video camera,
   identifying potential physical abuse from the video data, the identification of potential physical abuse being to within a predetermined confidence level, and
   transmitting information indicating that a potential human threat has been identified
   wherein identifying potential physical abuse comprises:
   tracking and modeling bodily motion of at least one person shown in the video data, including identifying and tracking 2D joint center positions of the at least one person;
   quantifying velocity and acceleration of at least one portion of a body of the at least one person shown in the video data using the tracked and modeled bodily motion; and
   determining potential physical abuse based on a comparison of the quantified velocity and acceleration of the at least one portion of the body of the at least one person shown in the video data with at least one threshold.

2. The system of claim 1, wherein the tracking and modeling bodily motion of the at least one person shown in the video data further comprises:
   predicting a motion of the at least one portion of the body of the at least one person shown in the video data on a 3D human model as joint angles of the at least one person over time.

3. The system of claim 1, wherein the predicting the motion of at the least one portion of the body comprises:
   connecting 2D joint center positions of the at least one person shown in the video data to form line segments.

4. The system of claim 1, wherein the at least one portion of the body comprises at least one of a wrist, a shoulder, an elbow, a foot, or a leg.

5. A method for identifying potential physical abuse, implemented in a computer comprising a processor, a memory accessible by the processor, and computer program instructions stored in the memory and executable by the processor, the method comprising:
    receiving video data from at least one video camera at a location;
    identifying potential physical abuse from the video data, the identification of potential physical abuse being to within a predetermined confidence level; and
    transmitting information indicating that a potential human threat has been identified,
    wherein identifying potential physical abuse comprises:
    tracking and modeling bodily motion of at least one person shown in the video data, including identifying and tracking 2D joint center positions of the at least one person;
    quantifying velocity and acceleration of at least one portion of a body of the at least one person shown in the video data using the tracked and modeled bodily motion; and
    determining potential physical abuse based on a comparison of the quantified velocity and acceleration of the at least one portion of the body of the at least one person shown in the video data with at least one threshold.

6. The method of claim 5, wherein the tracking and modeling bodily motion of the at least one person shown in the video data further comprises:
    predicting motion of the at least one portion of the body of the at least one person shown in the video data on a 3D human model as joint angles of the at least one person over time.

7. The method of claim 5, wherein the predicting the motion of the at least one portion of the body comprises:
    connecting 2D joint center positions of the at least one person shown in the video data to form line segments.

8. The method of claim 5, wherein the at least one portion of the body comprises at least one of a wrist, a shoulder, an elbow, a foot, or a leg.

* * * * *